Figure 1:
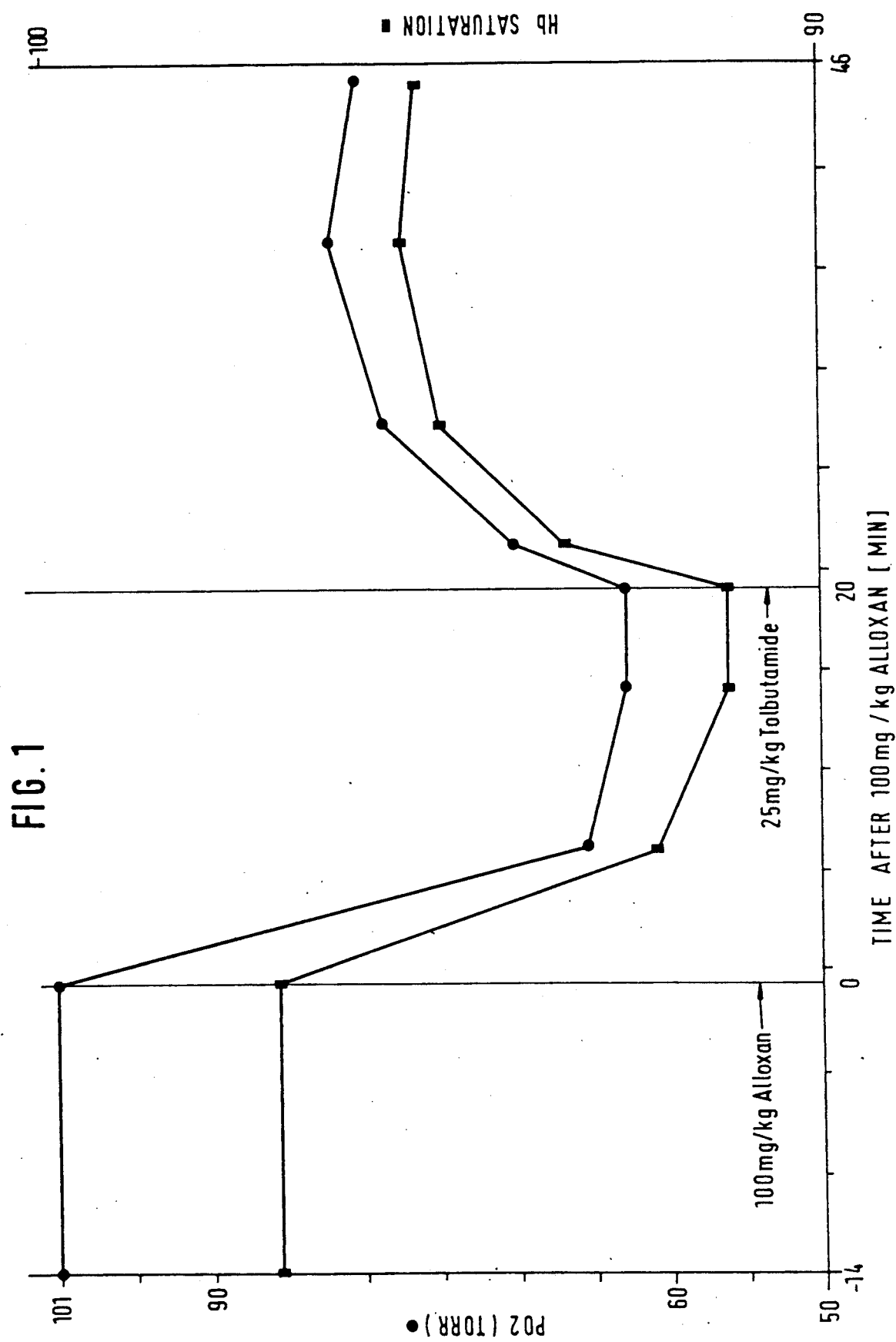

United States Patent [19]

Nye

[11] Patent Number: 5,047,429

[45] Date of Patent: Sep. 10, 1991

[54] TREATMENT OF OEDEMA

[75] Inventor: Piers C. G. Nye, Oxford, Great Britain

[73] Assignee: Hoechst Aktiengesellschaft, Frankfurt am Main, Fed. Rep. of Germany

[21] Appl. No.: 339,763

[22] Filed: Apr. 18, 1989

[30] Foreign Application Priority Data

Apr. 19, 1988 [GB] United Kingdom ................ 8809205

[51] Int. Cl.$^5$ ........................... A61K 31/175
[52] U.S. Cl. .................... 514/592; 514/593; 514/870
[58] Field of Search ......... 514/592, 593, 870

[56] References Cited

U.S. PATENT DOCUMENTS 2,968,158  1/1961  Ruschig et al. ............... 514/592

OTHER PUBLICATIONS

Chemical Abstracts (vol. 77: 135160n).
Chemical Abstracts (109:85908u).

*Primary Examiner*—Stanley J. Friedman
*Assistant Examiner*—Kevin E. Weddington
*Attorney, Agent, or Firm*—Finnegan, Henderson, Farabow, Garrett, and Dunner

[57] ABSTRACT

A method is described for treating and/or preventing pulmonary oedema in patients comprising administering a suphonylurea compound or a pharmaceutically acceptable salt thereof to patients who suffer from or are susceptible to oedema. Glucose may also be simultaneously administered to the patients to prevent hypoglycemia.

6 Claims, 1 Drawing Sheet

TREATMENT OF OEDEMA

The present invention is concerned with the use of a compound for the preparation of a medicament for the treatment and/or prevention of oedema.

Oedema is a condition in which an abnormal accumulation of serous fluid occurs, it is often associated with defective circulation although there are a number of other causes. Oedema can affect a variety of tissues. Pulmonary oedema can in particular be a life threatening complication of a variety of pathological disturbances of the cardiovascular and respiratory system. It is frequently seen in conditions of coronary vascular disease, left ventricular failure, mitral valve disease or as a result of therapeutic radiation of the lung or heroin overdose as well as a number of other conditions. Pulmonary oedema results in a severe drop in the oxygen content of the blood due to fluid in the lung acting as a diffusion barrier between gas in the lungs and the blood with which that gas normally equilibrates. Pulmonary oedema can be fatal in a matter of minutes and there exists a need for an effective means to rapidly treat the condition eg by removing the fluid from the lung.

This need is met by the present invention by the use of a medicament comprising a sulphonylurea compound.

The sulphonylureas are oral hypoglycemic agents used extensively for the treatment of non-insulin-dependent diabetes. They stimulate the pancreatic islet cells (beta cells) to secrete insulin. They have been shown to block ATP sensitive potassium channels in the membranes of these cells. It is thought that glucose normally closes these channels by raising intracellular ATP and that this is the key link between raised levels of plasma glucose and the secretion of insulin. Sulphonylureas have been found to have few effects outside their action on the pancreas. They are known to inhibit release of catecholamines by the adrenal medulla but are not known to have any effect on the lung or on oedema. Examples of sulphonylurea compounds include:
  tolbutamide
  tolazamide
  acetohexamide
  chlorpropamide
  glyburide
  glipizide
  glibornuride
  glicazide
  gliquidone As used herein the term sulphonylurea compounds includes also pharmaceutically acceptable salts, eg sodium tolbutamide.

One aim of the present invention is to provide a means to rapidly remove the accumulation of oedemous fluid. This aim may be achieved by the administration of a medicament comprising a sulphonylurea compound or pharmaceutically acceptable salt thereof. In order to provide acute relief the medicament is usually administered by injection intravenously, for which purpose water soluble salts generally need to be used.

However it is also known that certain subjects for example persons suffering from circulatory disease are susceptible to pulmonary oedema. The long term administration of medicaments comprising sulphonylurea compounds for the prevention of oedema is also within the scope of this invention. Sulphonylurea compounds have been shown to be adequately safe for long term administration in many diabetics. Long term administration may best be by oral route.

Since the sulphonylureas are known antidiabetic agents their administration for the treatment of oedema may result in hypoglycemia. It is therefore envisaged that medicaments including sulphonylurea compounds for the treatment of oedema may also include glucose or be administered in conjunction with glucose.

Doses of sulphonylureas may range from 5mg up to 5g depending on the sulphonylurea compound used. Doses for long term administration would desirably be less than for acute relief preferably in the range from 2.5mg to 2g per day depending on the particular sulphonylurea compound used.

The present invention will now be illustrated by experimental example. Measurement of partial arterial oxygen pressure (PaO2) is a measure of the oxygen dissolved in the blood and hence the degree to which pulmonary oedema has affected gas diffusion. A lower PaO2 indicates that gas diffusion is inhibited by the oedemous fluid.

A subjective estimation of the degree of pulmonary oedema can be obtained by placing a microphone over the entrance to the airways to the lung. The presence of fluid on the lungs causes audible sounds when breathing. A reduction in the sound is an indication of removal of oedemous fluid from the lungs.

Due to the difficulty in consistently producing pulmonary oedema the drug alloxan, which is known to induce pulmonary oedema, was used in some experiments.

EXAMPLE 1

The PaO2 of a fluorothene anesthetized rabbit breathing 97.5% $O_2$ and 2.5% fluorothane was determined periodically. At such a concentration of oxygen the PaO2 would be expected to be approximately 400 Torr. However the PaO2 was only 75 to 80 Torr and in addition audible sounds occurred each time the animal breathed. This clearly indicates the animal was suffering from spontaneous pulmonary oedema. After 1 hour, 25mg/kg of tolbutamide was injected intravenously. Within 10 minutes the PaO2 was increased to 240 Torr and audible sounds from the lungs had ceased. A further measurement of PaO2 taken 10 minutes later gave a PaO2 of 220 Torr confirming the relief of the pulmonary oedema.

EXAMPLE 2

Two cats were anesthetized with pentobarbitone and microphones attached to the entrance of the lung airways. The animals were breathing normal air. After allowing the animals to stabilize for a period 100mg/kg of alloxan was administered iv. This produced a reduction in PaO2 of about 40 Torr and in addition sounds from the lungs were detected by the microphone during breathing. 20 minutes after administration of the alloxan the animals were given 25mg/kg tolbutamide. Within 2 minutes PaO2 increased by 7 Torr and by 16 Torr in 8 minutes. In addition a simultaneous reduction in the amplitude of the sound detected by the microphone was noted. Administration of 100mg/kg alloxan is invariably fatal to a cat within 1 hour but one cat was given three 100mg/kg closes of alloxan followed by tolbutamide and survived for 1.5 hours.

FIG. 1 shows the partial arterial oxygen pressure and percentage saturation of one of these animals during the course of the experiment.

I claim:

1. A method of treating pulmonary oedema in a patient comprising administering to said patient an oedemous-fluid- removing effective amount, a sulphonylurea compound or a pharmaceutically acceptable salt thereof.

2. The method of claim 1 wherein said sulphonylurea compound is tolbutamide (N-Butyl-N'-toluene-p-sulphonylurea).

3. The method of claim 1 further comprising administering an amount of glucose sufficient to prevent hypoglycemia together with said sulphonylurea compound.

4. A method of preventing pulmonary oedema in a patient susceptible to pulmonary oedema comprising administering to said patient an effective amount of sulphonylurea compound or a pharmaceutically acceptable salt thereof, wherein said amount is sufficient to prevent pulmonary oedema.

5. The method of claim 4 wherein said sulphonylurea compound is tolbutamide (N-Butyl-N'-toluene-p-sulphonylurea).

6. The method of claim 4 further comprising administering an effective amount of glucose together with said sulphonylurea compound.

* * * * *